United States Patent [19]

Mussi et al.

[11] Patent Number: 5,527,705
[45] Date of Patent: Jun. 18, 1996

[54] ROLLER BOTTLE FOR TRANS-MEMBRANE CO-CULTURE OF CELLS AND METHOD FOR ITS USE

[75] Inventors: Edward F. Mussi, Hewitt; Harry E. Gray, Woodbridge, both of N.J.

[73] Assignee: Becton, Dickinson and Company, Franklin Lakes, N.J.

[21] Appl. No.: 304,463

[22] Filed: Sep. 12, 1994

[51] Int. Cl.$^6$ .......................... C12M 3/00; C12M 1/24; C12N 5/00; B65D 90/04
[52] U.S. Cl. ................. 435/297.1; 435/240.241; 435/240.242; 435/299.2; 435/304.2; 220/4.13; 220/400; 220/404; 220/413; 220/426; 220/660; 220/661; 220/662; 220/DIG. 14
[58] Field of Search ................... 435/284, 296, 435/300, 312, 240.241, 240.242; 220/4.13, 400, 404, 413, 426, 660, 661, 662, DIG. 14

[56] References Cited

U.S. PATENT DOCUMENTS

| | | | |
|---|---|---|---|
| 3,941,661 | 3/1976 | Noteboom | 197/127 |
| 4,238,568 | 12/1980 | Lynn | 435/285 |
| 4,308,351 | 12/1981 | Leighton et al. | 435/284 |
| 4,337,104 | 6/1982 | Lynn | 156/69 |
| 4,350,575 | 9/1982 | Porta et al. | 204/84 |
| 4,830,970 | 5/1989 | Madaus et al. | 435/296 |
| 4,912,058 | 3/1990 | Mussi et al. | 435/285 |
| 5,139,953 | 8/1992 | Honda et al. | 435/312 |
| 5,260,210 | 11/1993 | Rubin et al. | 435/240.242 |

OTHER PUBLICATIONS

Miller et al, Application of Cultured Endothelial Cells of the Brain Microvasculature in the Study of the Blood–Brain Barrier, J. Tiss. Cult. Meth. 14:217–224, 1992.

Madara et al, A Simple Approach to Measurement of Electrical Parameters of Cultured Epithelial Monolayers: Use in Assessing Neutrophil–epithelial Interactions, J. Tiss. Cult. Meth. 14:209–216, 1992.

Mangum et al, Co–Culture of Primary Pulmonary Cells to Model Alveolar Injury and Translocation of Proteins, In Vitro Cell. Dev. Biol. 26:1135–1143, Dec. 1990.

C. Grobstein, Trans–Filter Induction of Tubules in Mouse Metanephrogenic Mesenchyme, Experimental Cell Research, 10, 424–440.

Frontiers in biology: Development, Looking to Development's Future, Science, vol. 266, 28 Oct. 1994, 561–570.

*Primary Examiner*—Donald E. Czaja
*Assistant Examiner*—Jane Williams Elkin
*Attorney, Agent, or Firm*—Arthur D. Dawson

[57] ABSTRACT

A roller bottle for trans-membrane co-culture of cells includes an exterior receptacle with a longitudinal axis having a first chamber surrounded by a sidewall. The exterior receptacle has a first neck at one end having an opening therethrough providing fluid access to said first chamber. The roller bottle further includes an interior container with a longitudinal axis and a second chamber, the interior container being located coaxially within the exterior receptacle. The interior container has a second neck at one end providing fluid access to the second chamber. The exterior receptacle is formed from a material that is substantially impermeable to gas and liquid and is sealed in a substantially fluid tight fashion forming the first chamber that has fluid access by the first neck. At least a portion of the interior container is formed from a microporous material. The roller bottle of the invention enables culturing one cell type in the presence of another cell type for the study of interactions between the cells while maintaining a physical separation between the cell types providing a scale up in cell population size from well type inserts. The microporous membrane allows free interchange of media soluble cellular products between the cell types, but maintains physical separation.

15 Claims, 6 Drawing Sheets

ROLLER BOTTLE FOR TRANS-MEMBRANE CO-CULTURE OF CELLS AND METHOD FOR ITS USE

BACKGROUND OF THE INVENTION

1. Field of the Invention

The present invention is generally related to culturing of cells and more particularly to a roller bottle suitable for trans-membrane co-culturing of cells.

2. Description of Related Information

Culturing of cells of various types has become a routine process in many laboratories. Cells are grown to harvest compounds, to test for various sensitivities to potentially toxic compounds and even to provide tissue for grafts. More recently, cells of different types have been co-cultured on opposite sides of a microporous membrane for the study of interactions between one type of cell and another. The function of the microporous membrane is to prevent physical contact of one cell type with the other cell type while allowing a chemical communication between the cell types using the cellular metabolites and cellular products soluble in the aqueous media. This procedure is called "trans-membrane co-culture."

Representative references to the co-culture of cells include Mangum et al., In Vitro *Cell Dev. Biol.* 26:1135–1143 (Dec., 1990) in which the authors describe a "Co-Culture of Primary Pulmonary Cells to Model Alveolar Injury and Translocation of Protein"; and Madara et al. in *J. Tissue Cult. Method.* 14:209–216, (1992) report "A Simple Approach to Measurement of Electrical Parameters of Cultured Epithelial Monolayers: Use in Assessing Neutrophil-Epithelial Interactions." Both of these papers and the references therein report a technique for growing cells of two different types on opposite sides of a suspended microporous membrane to study the interactions between the cells. Madara et al. provide a detailed report of a trans-membrane co-culture study. Madara et al. also describe modifications of a commercial cell culture insert by adhesively bonding a machined polycarbonate ring onto the underside of the insert to facilitate the growth of monolayers on both sides of the membrane. These modifications of an existing product described by Madara et al., provided them with a way to conduct a small scale experiment on interactions of two types of cells, but the equipment developed by Madara et al. is not suitable for larger scale studies.

As the technique of trans-membrane co-culture of cells becomes of greater interest, there is a need to grow larger populations of co-cultured cells than can easily be handled using small (1–5 cm.) well insert apparatus. One example demonstrating the need for larger scale co-culture is that some types of cellular metabolite products are secreted by one type of cells only in the presence of other types of cells. These metabolite products are produced in very small quantities in a co-culture of the cells. The effect of these metabolites from one cell type on another cell type may be observed in the small well insert apparatus, but in order to isolate sufficient quantities of these metabolites for detailed characterization, it is desirable to grow larger populations of the co-culture cells.

In scale up of cell monocultures, the containers used in laboratory settings for cell culturing are commonly known as "roller bottles." These roller bottles are generally cylindrical and are adapted to rotate about their longitudinal axis when placed on a laboratory roller apparatus. The laboratory roller apparatus is often adapted to fit within chambers for controlling the temperature and atmosphere. The bottles have evolved into standard sizes of about 0.85, 1.75 and 3.5 liters capacity and about 11–12 cm. in diameter because of the constraints of the roller apparatus.

The most common application for these bottles is to be charged with a few hundred milliliters (ml) of aqueous growth medium containing a suspension of the cells to be cultured. The bottles are placed on their sides on a laboratory roller apparatus, generally in a temperature and atmosphere controlled environment, so that a longitudinal portion of the inside surface of the bottle is always wet by the growth medium, and rotated slowly (about 1–2 rpm) about their axis for several days. During this time, the cells grow and utilize the nutrients present in the growth medium, generally by attaching themselves to the surface of the bottle. In many applications, it is necessary to drain and recharge the growth medium during the course of the growth cycle, either to harvest by-products, remove waste or replenish nutrients.

There is a need for devices similar to mono-culture roller bottles for scaling up of trans-membrane co-culture systems. Such a device and a method for its use are described below.

SUMMARY OF THE INVENTION

A preferred roller bottle for trans-membrane co-culture of cells includes an exterior receptacle with a longitudinal axis having a first chamber surrounded by a sidewall with a first neck at one end having an opening therethrough providing fluid access to the chamber. The roller bottle further includes an interior container with a longitudinal axis and a second chamber, the interior container being located coaxially within the exterior receptacle. The interior container has a second neck at one end having an opening therethrough providing fluid access to the second chamber. The exterior receptacle preferably is formed from a material that is substantially impermeable to gas and liquid. Preferably, the exterior receptacle is sealed in a substantially fluid tight fashion forming the first chamber having fluid access from the first neck. At least a portion of the interior container is preferably formed from a microporous material. The interior container is sealed in a substantially fluid tight fashion forming the second chamber. The second chamber has fluid access from the second neck at the second end of the interior container.

A preferred method for trans-membrane co-culture in a roller bottle includes charging a first chamber in an exterior receptacle of a roller bottle with a first population of cells in a first suitable liquid growth medium for propagation of those cells so that the liquid forms a layer covering at least a portion of a sidewall of the exterior receptacle when the bottle is placed horizontally. The preferred method then includes closing the first chamber, horizontally placing the roller bottle having the first medium and the first population of cells for a sufficient time in an environment suitable for propagation of the cells and allowing the first population of cells to propagate. Preferably, the bottle is removed from the environment followed by charging a second chamber of the roller bottle with a second population of cells in a suitable second liquid medium for propagation of the second population of cells. Preferably, the second chamber is in an interior container located within the exterior receptacle, the interior container preferably having a sidewall formed from a microporous membrane allowing fluid communication between the first chamber and the second chamber while substantially preventing physical contact between the first population of cells and the second population of cells. Preferably, the second chamber is then closed and the roller bottle having the first medium and the first population in the first chamber and the second population and the second medium in the second chamber is horizontally placed in an environment suitable for propagation of the populations. As the cells propagate, the environment of each population is changed by the presence of the other population because cellular metabolites soluble in the aqueous media are freely transmitted through the membrane. The membrane functions to keep the two populations physically separate. The physical separation allows harvesting the individual populations of the cells and control of the cellular communication. The bottle is preferably left in the environment for a sufficient time for allowing the second population of cells to propagate in fluid communication with the first population of cells.

The roller bottle of the present invention provides a device useful to scale-up a trans-membrane co-culture of one or more populations of living cells and a method for its use. Prior to the invention of this device and method, the only way believed to increase the production of a trans-membrane co-culture of two populations of cells was to set up multiples of a small well type apparatus. Since each individual co-culture requires separate handling and manipulation, maintaining multiple co-cultures is labor intensive and prone to variability. The roller bottle of the present invention provides a simple, easily used device and method for its use for larger scale trans-membrane co-culture than existent well type apparatus. The art of cell culture is advanced by the present invention that enhances the ability to produce larger populations of co-cultured cells as interest in the technique develops and permits wider use of co-culture.

DETAILED DESCRIPTION OF THE INVENTION

Figure 1:
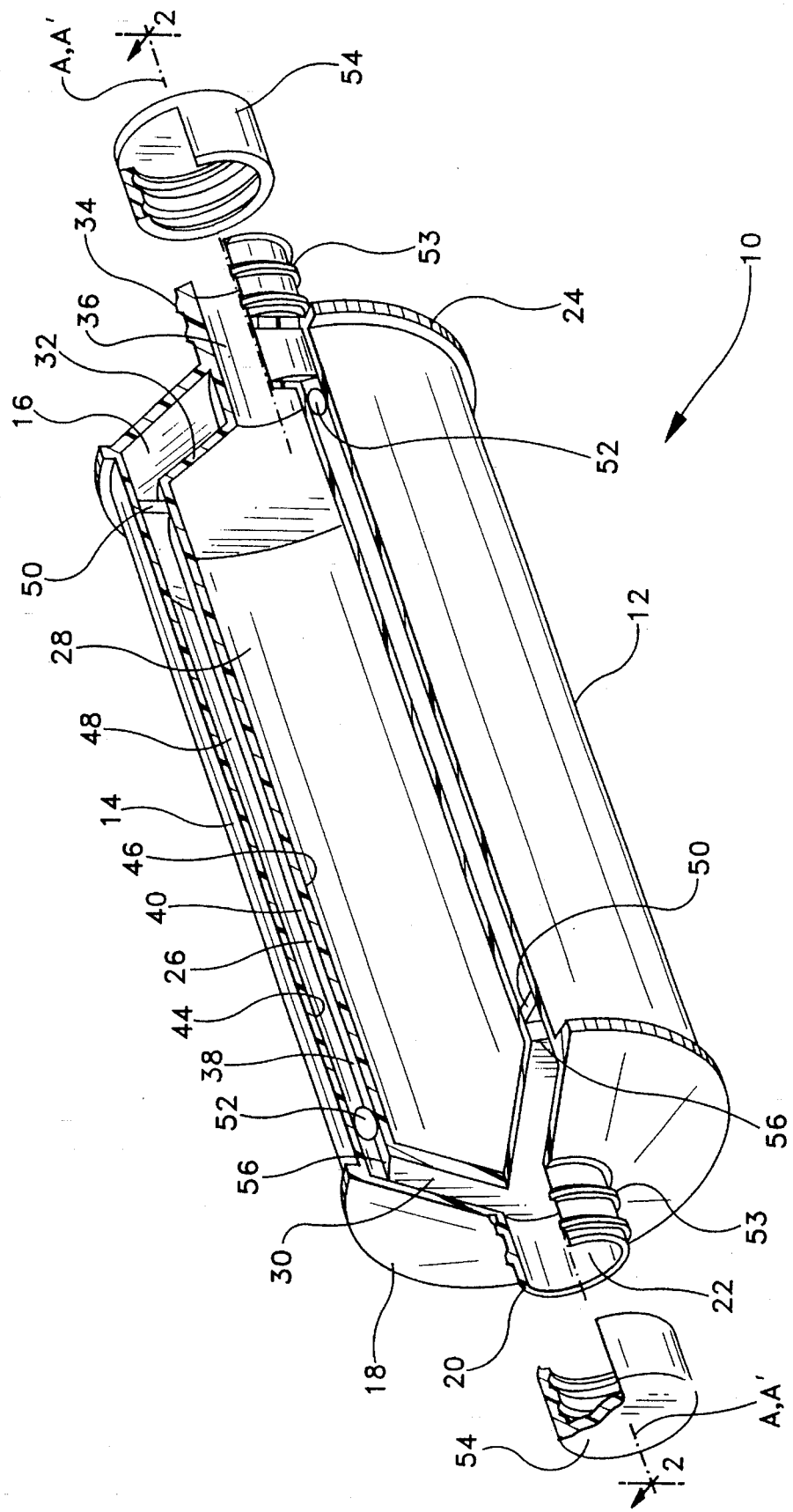
FIG. 1 is an exploded partial cut-away perspective view of a preferred embodiment of the present invention.

While this invention is satisfied by embodiments in many different forms, there is shown in the drawings and will herein be described, several embodiments of the invention with the understanding that the present disclosure is to be considered as exemplary of the principles of the present invention and is not intended to limit the scope of the invention to the embodiments illustrated. The scope of the invention will be measured by the appended claims and their equivalents.

Figure 2:
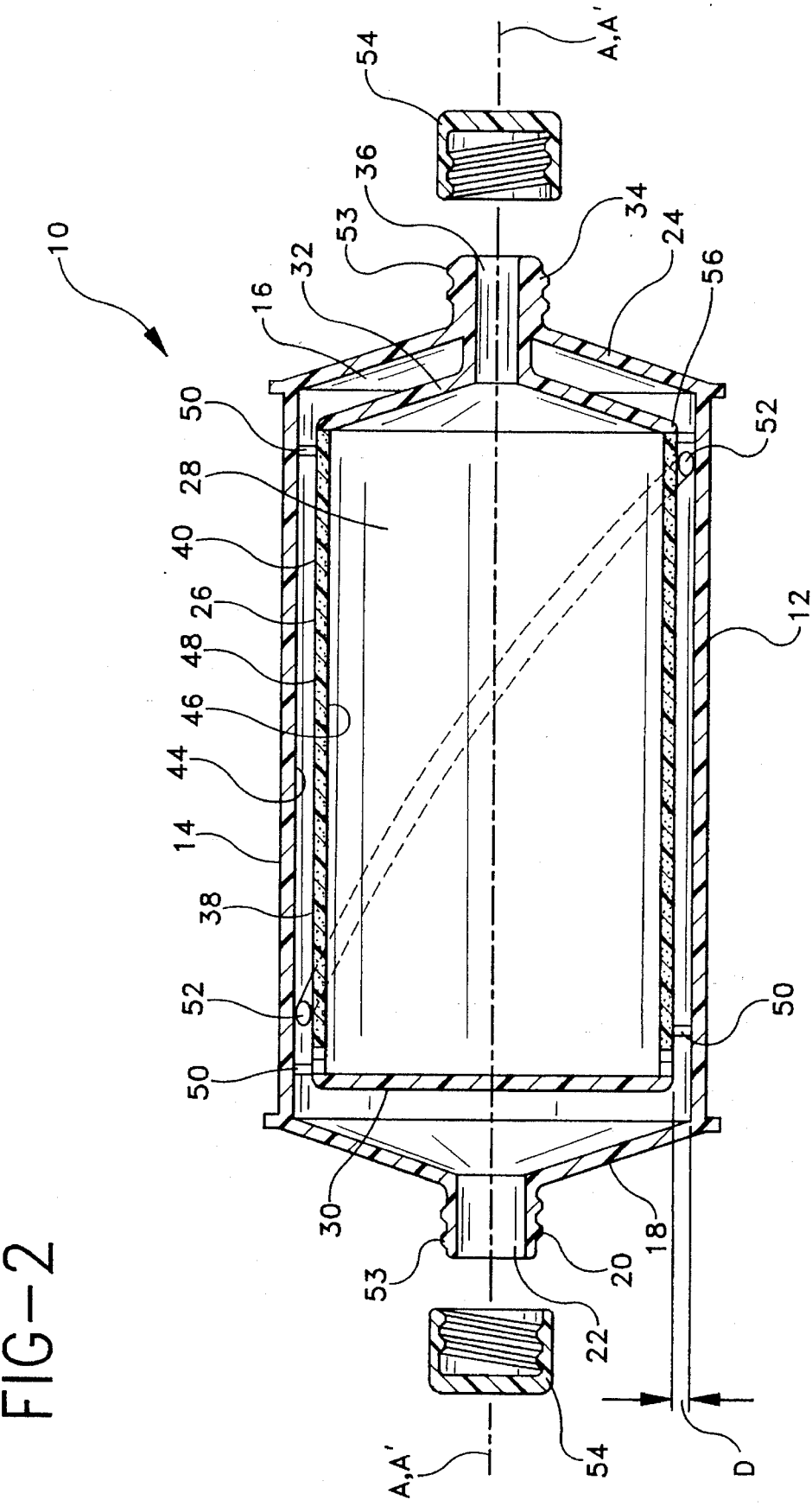
FIG. 2 is a cross sectional view of the roller bottle of FIG. 1 taken along the line 2—2.

As shown in FIGS. 1 and 2, a roller bottle 10 for trans-membrane co-culture of cells preferably includes a generally cylindrical exterior receptacle 12 with a longitudinal axis A and a sidewall 14. Exterior receptacle 12 has a first chamber 16 within, and first end 18 having a first neck 20 with a neck opening 22 therethrough providing fluid access to first chamber 16. Exterior receptacle 12 includes a second end 24.

Roller bottle 10 preferably includes a generally cylindrical interior container 26 having a second chamber 28 within and a longitudinal axis A'. Preferably interior container 26 is located coaxially within exterior receptacle 12 and has a first end 30 adjacent to first end 18 of exterior receptacle 12 and a second end 32 adjacent to second end 24 of the interior container. First end 30 preferably is recessed from first end 18 of the exterior container to provide clearance for adding and withdrawing fluid from first chamber 16. Second end 32 of the interior container and second end 24 of the exterior receptacle have a second neck 34 having an opening 36 therethrough for providing fluid access to second chamber 28. Opening 36 in second neck 34 is isolated from first chamber 16, so that second neck 34 provides fluid access only to second chamber 28.

Exterior receptacle 12 is preferably formed from a material substantially impermeable to gas and liquid and is sealed in a substantially fluid tight fashion at first end 18 and second end 24 forming first chamber 16 with fluid access from first neck 20 at first end 18. At least a portion 38 of interior container 26 is preferably formed from a microporous material. Preferably interior container 26 has a sidewall 40 formed from the microporous material.

In the art of cell mono-culture, it is well-accepted usage of a roller bottle for the bottle to be placed on a laboratory roller system with its longitudinal axis horizontal and then rotated slowly (ca. less than 5 rpm) about the longitudinal axis. Generally an amount of aqueous liquid growth medium sufficient to cover a portion of the longitudinal sidewall surface is introduced into the bottle through the neck. The growing cells attach themselves to an inside surface of exterior sidewall and proliferate. In roller bottle 10 of the present invention for cell co-culture, both exterior receptacle 12 and interior container 26 have interior surfaces. Exterior receptacle 12 has an inside surface 44 and interior container sidewall 40 has an inside surface 46 and an outside surface 48. Interior container 26 is preferably coaxially supported within exterior receptacle 12 so that interior sidewall outside surface 48 is maintained a distance D from inside surface 44 of the exterior sidewall. Preferably distance D is between about 0.010 inches (0.254 millimeters) to about 0.40 inches (10.16 millimeters). Distance D is preferably maintained by support members 50 that support interior container 26 within exterior receptacle 12. Support members 50 preferably include at least one helical support member 52 extending from first end 30 to second end 32 of the interior bottle.

Helical support member 52 preferably functions as an Archimedes screw as bottle 10 is horizontally rotated about its longitudinal axis when the exterior receptacle has a layer of aqueous liquid growth medium in first chamber 16, lifting the medium contained in first chamber 16, providing gentle mixing and maintaining a flow of medium over outside surface 48 of the interior container.

Suitable materials for the microporous membrane include but are not limited to polymeric materials such as polyethylene terephthalate, polycarbonate and the like with open pores therethrough. Preferably the membrane is about 20 microns to about 30 microns thick and the pores are between about 0.2 microns to about 10 microns in diameter with a pore density between about $0.1 \times 10^6$ to about $10.0 \times 10^6$ pores per square centimeter. Preferred microporous membranes include the track-etched membranes supplied by, but are not limited to, "Cyclopore™" (Avenue Einstein, Louvain-la- Neuve, Belgium) and "Poretics™" (Livermore, Calif.) The microporous membrane serves to allow fluid communication between a first population of cells in the first chamber and a second population of cells in the second chamber while substantially preventing physical contact between the populations of cells.

Preferably, first neck 20 at the first end of the exterior receptacle and second neck 34 at the second end of the exterior receptacle include male threads 53 and are sized similarly to the neck configuration of standard commercial roller bottles allowing the use of standard closures 54 for roller bottles.

Preferably sidewall 14 of exterior receptacle 12 is formed from a plastic resin that may be a thermoplastic including polypropylene, polycarbonate, polyurethane, polyvinyl chloride, polymethyl methacrylate, polystyrene, polyethylene terephthalate, polyester and the like. Most preferably sidewall 14 is extruded from crystalline polystyrene. Inner surface 44 of sidewall 14 may have a surface treatment to enhance the facility of cell attachment. Such treatments may include, but are not limited to, plasma treatment, corona discharge treatment, surface oxidation and the like.

Exterior receptacle first end 18 and second end 24 preferably are formed from a thermoplastic resin such as polypropylene, polycarbonate, polyurethane, polyvinyl chloride, polymethyl methacrylate, polystyrene, polyethylene terephthalate, polyester and the like and most preferably are formed by an injection molding process from polystyrene. Interior container first end 30, support members 50 and helical support member 52 may be formed from a thermoplastic resin such as polypropylene, polycarbonate polyurethane, polyvinyl chloride, polymethyl methacrylate, polystyrene, polyethylene terephthalate, polyester and the like. Preferably the interior container components including first end 30, helical support member 52, support members 50 and one exterior receptacle component, second end 24, are formed from polystyrene and bonded together to form a framework 56 for the interior container. The components forming interior framework 56 may be bonded together by adhesive bonding, solvent bonding, ultrasonic welding, thermal bonding or any other method for providing a secure bond. Preferably the components for framework 56 are bonded together by solvent bonding. Porous membrane portion 38 preferably forms sidewall portion 40 of the interior container with the porous membrane being bonded to framework 56 by adhesive bonding, solvent bonding, ultrasonic welding, thermal bonding or any other method for providing a substantially fluid tight attachment between the membrane and the framework. It is preferred that the bonding be substantially fluid tight so that cells in one chamber cannot be commingled with cells from the other chamber. All fluid communication between the first chamber and the second chamber preferably occurs through the microporous membrane that substantially prevents the passage of cells. Preferably the membrane is bonded to framework 56 by solvent bonding.

Preferably the entire interior container 26 is preassembled including the exterior receptacle second end, as described above, and then finally coaxially assembled with exterior receptacle sidewall 14 being bonded to exterior receptacle second end 24 and exterior receptacle first end 18 to complete the assembly of the roller bottle as shown in FIGS. 1 and 2. Adhesive bonding, solvent bonding, ultrasonic welding, thermal bonding or any other method providing a substantially fluid tight attachment may be used to attach the ends to the sidewall. For the most preferred embodiment of the exterior bottle, where the exterior receptacle sidewall and both exterior receptacle ends are polystyrene, solvent bonding is preferred.

A preferred method for using roller bottle 10 of the present invention to culture two populations of cells physically separate from each other but in fluid chemical communication includes charging first chamber 16 in exterior receptacle 12 with a first population of cells in a first liquid growth medium suitable for propagation of the first population. Preferably, sufficient liquid is used so that the liquid forms a layer covering at least a portion of sidewall interior surface 44 of the exterior receptacle when the bottle is placed horizontally. The chamber is then preferably closed and bottle 10 with the medium and the first cell population is then placed horizontally in an environment suitable for the cells' propagation. Preferably, bottle 10 is axially rotated between about one to about 5 rpm to gently stir the medium and bathe the cells on the sidewall with the liquid medium. When the first cell population has increased to the desired level, generally formation of a confluent layer on the exterior container's interior sidewall surface is desired, a second population of cells in a second liquid growth medium is charged into second chamber 28 of interior container 26 that preferably has sidewall 40 formed from a microporous material. Preferably, a sufficient amount of the second liquid medium is used so that the liquid forms a layer covering at least a portion of interior container sidewall inside surface 46 when bottle 10 is horizontal. Bottle 10 is then placed horizontally in an environment suitable for propagation of both cell populations and again rotated slowly to provide stirring and bathe the cells on both sidewalls with the media.

One alternate method for using bottle 10 to the method described above would be to concurrently charge first chamber 16 with one cell type in the appropriate medium and second chamber 28 with another cell type in the appropriate medium. Bottle 10 may then be placed in the desired environment and the cell populations allowed to propagate. Another alternate method would be to charge second chamber 28 with one cell type in the appropriate medium, allow those cells to propagate to a desired level in the interior container and then charge first chamber 16 with another population of cells in the appropriate medium, followed by allowing the cells in both chambers to propagate as a co-culture.

In the present description, the term "trans-membrane co-culture" is intended to include, but is not limited to, the following applications in analogy to those applications commonly performed using well-type insert systems.

a) Monoculture as a monolayer of one population of cells on the inner surface of the interior container, this application provides the ability to provide medium contact with the growing cells on both the apical and basolateral surface.

b) Co-culture with one monolayer of a first population of cells on the inner surface of the external receptacle and one monolayer of a second population of cells on the inner surface of the interior container.

c) Co-culture with one monolayer of a first population of cells on the inner surface of the interior container and one monolayer of a second population of cells on the outside surface of the interior container.

d) A three component culture with one monolayer of a first population of cells on the inner surface of the interior container, one monolayer of a second population of cells on the outside surface of the interior container and one monolayer of a third population of cells on the inside surface of the exterior receptacle.

FIGS. 3, 4, 5 and 6 show alternate embodiments to the roller bottle shown in FIGS. 1 and 2. In these embodiments, there are elements similar in structure and function to the embodiment of the present invention shown in FIGS. 1 and 2. Accordingly, substantially similar components that perform substantially similar functions are numbered identically to those components of the embodiment of FIGS. 1 and 2 except that suffixes are used to identify those components in FIGS. 3 through 6 respectively.

Figure 3:
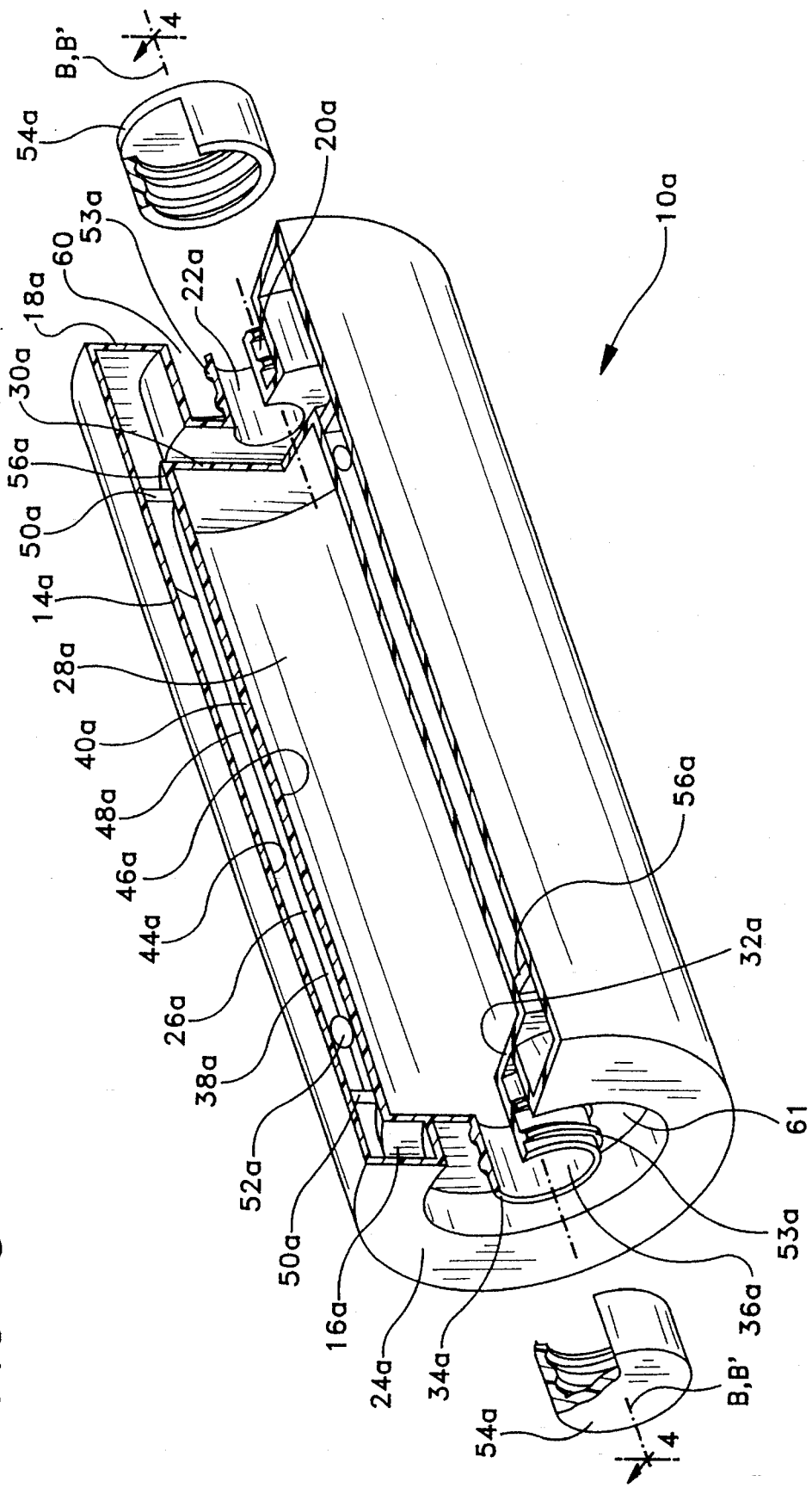
FIG. 3 is an exploded partial cut-away perspective view of an alternate embodiment of the present invention.
Figure 4:
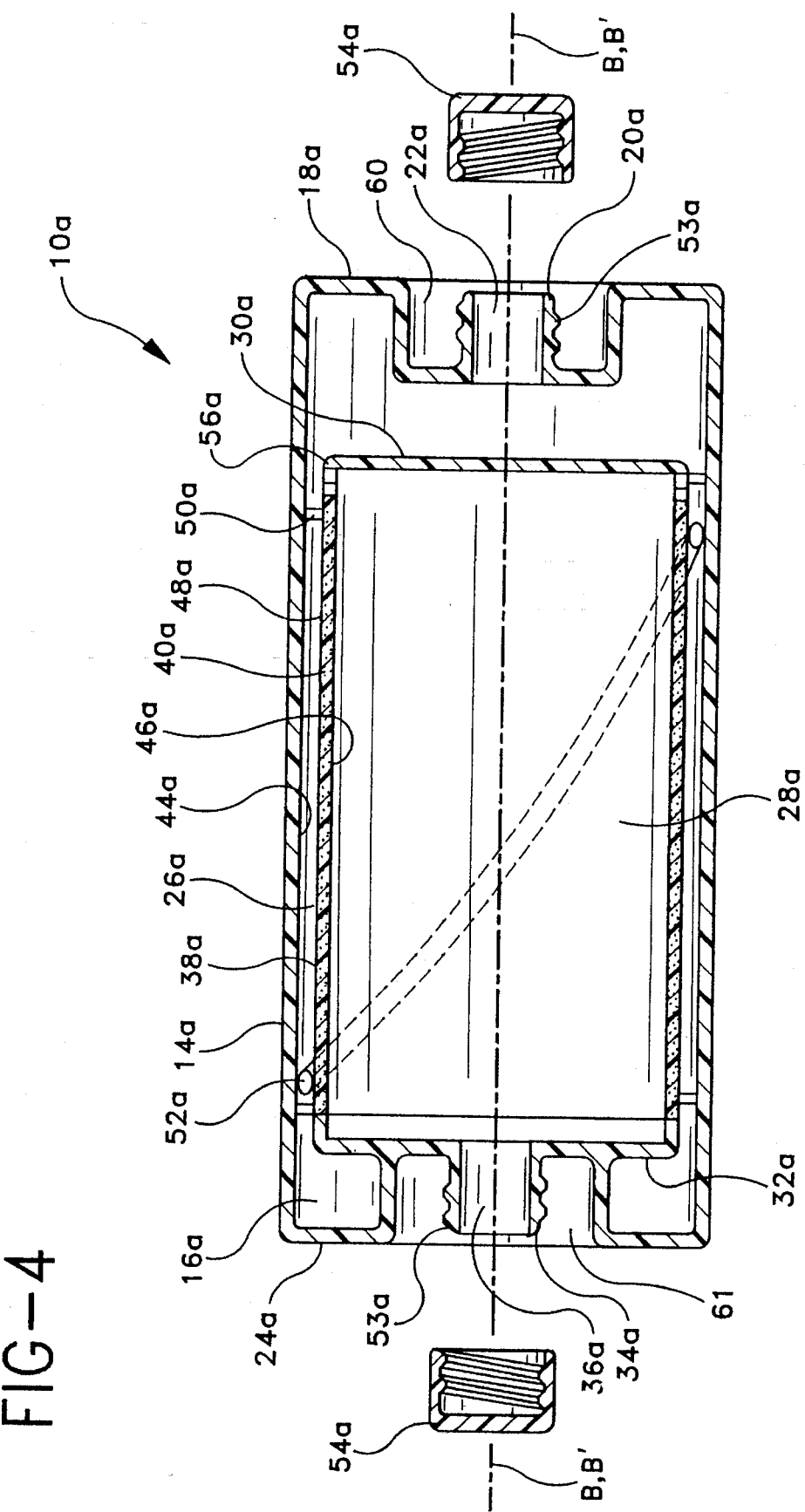
FIG. 4 is a cross sectional view of the roller bottle of FIG. 3 taken along the line 4—4.
Figure 5:
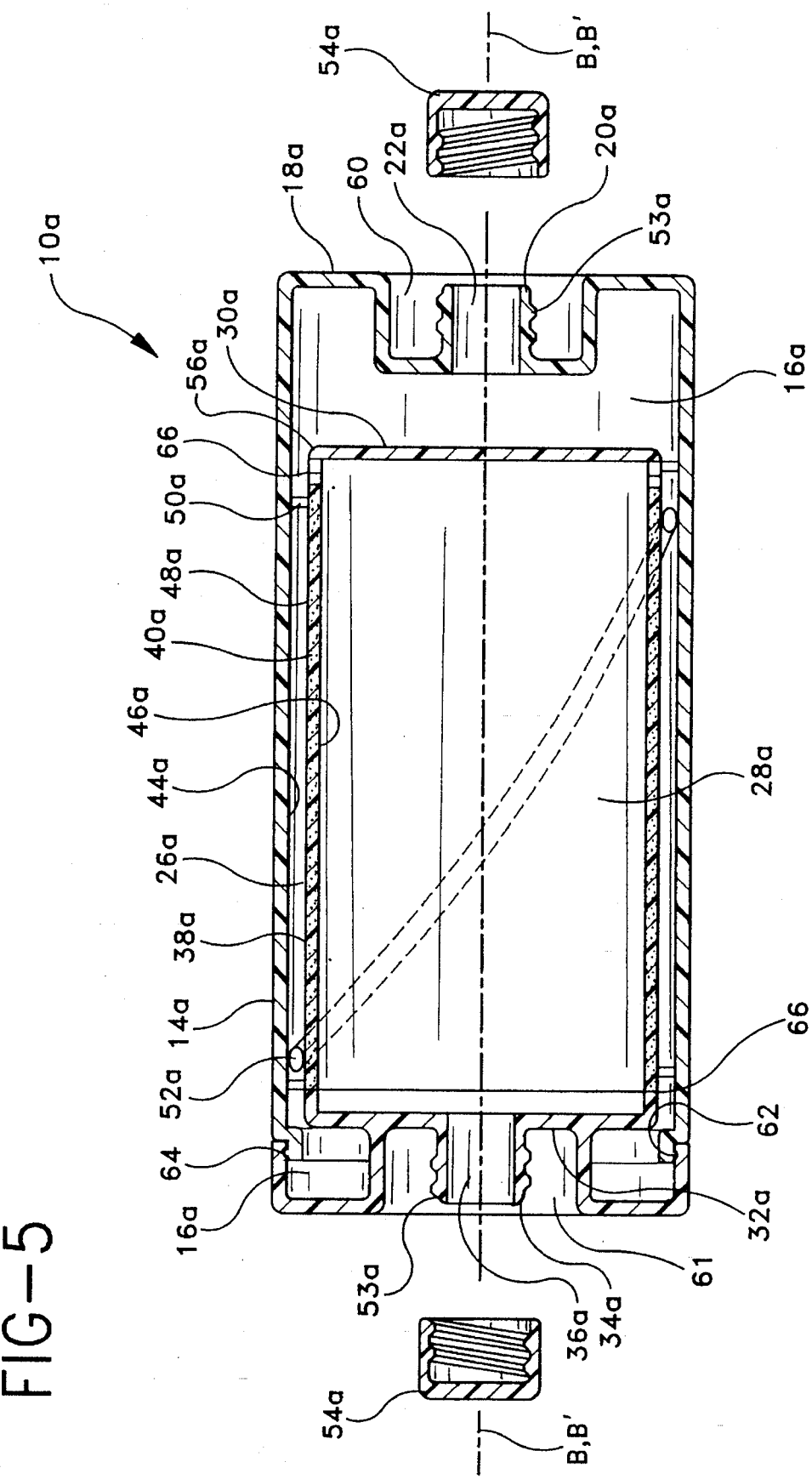
FIG. 5 is a cross sectional view of another alternate embodiment of the roller bottle of FIG. 3.

As shown in FIGS. 3, 4 and 5, roller bottle 10a for trans-membrane co-culture of cells includes a generally cylindrical exterior receptacle 12a with a longitudinal axis B and a sidewall 14a. Preferably, exterior receptacle 12a has a first chamber 16a within and first end 18a having a first neck 20a with a neck opening 22a set in a recess 60 providing access to chamber 16a. Recess 60 enables bottle 10a to stand upright on first end 18a to facilitate handling and reduce space requirement on the rollers.

Roller bottle 10a preferably includes generally cylindrical interior container 26a with a longitudinal axis B' having a second chamber 28a within. Preferably interior container 26a is located coaxially within exterior receptacle 12a and has an end 30a adjacent to first end 18a of exterior receptacle 12a and a second end 32a adjacent to second end 24a of the exterior receptacle. Second end 32a of the interior container and second end 24a have a second neck 34a having an opening 36a therethrough for providing fluid access to second chamber 28a. In this embodiment, neck 34a is preferably placed in a recess 61 so that even when a cap 54a is in position on the second neck, bottle 10a may stand upright on second end 24a.

As shown in FIGS. 3, 4 and 5, bottle 10a preferably is formed and assembled as described for the embodiment shown in FIGS. 1 and 2. As shown in FIG. 5, bottle 10a may further include elements 64 on exterior receptacle second end 24a to mate with elements 62 on sidewall 14a to releasably retain second end 24a on sidewall 14a. Elements 64 may include but are not limited to snap-fit fittings, threads and the like, with elements 62 being cooperative snap-fittings, threads and the like respectively. The particular form of the cooperating elements, 62 and 64, is not critical to the invention. Any fitting that readily forms a substantially fluid tight seal between second end 24a and sidewall 14a without interfering with rotation of bottle 10a on a laboratory roller would be satisfactory. In this embodiment, since interior container 26a is removable from exterior receptacle 12a, membrane portion 38a may be attached to framework 56a with easily removed attachment 66 so that membrane 38 may be removed to allow access to the cells growing on inside surface 46a of the membrane. Attachment 66 may include, but is not limited to, a reduced thickness edge, a peelable adhesive, mechanical press-fit with a sealing ring and the like.

Figure 6:
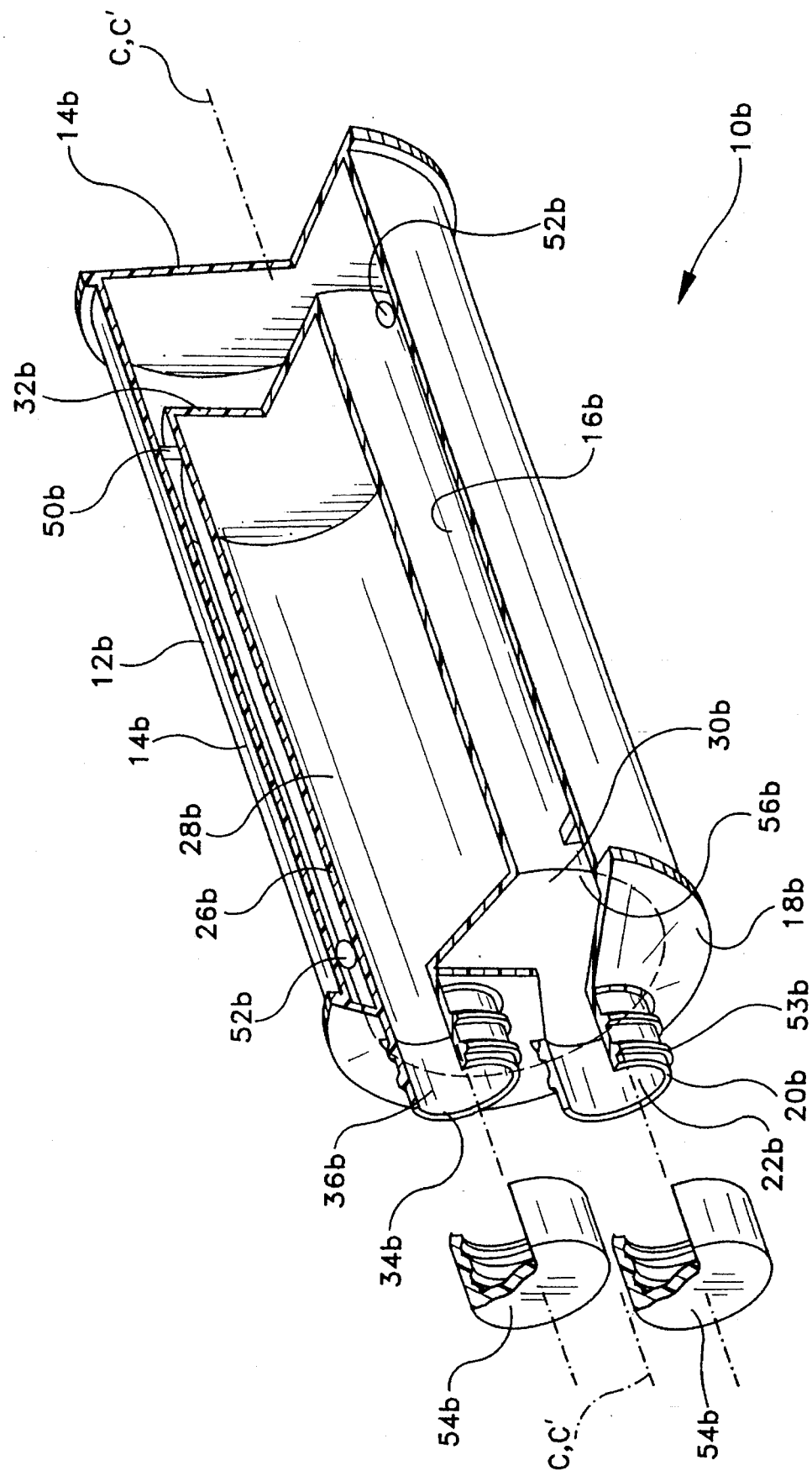
FIG. 6 is an exploded partial cut-away perspective view of a further alternate embodiment of the present invention.

Another alternate embodiment 10b of the present invention is shown in FIG. 6. In this embodiment, all features of the embodiments shown in FIGS. 1–5 may be retained with similar function, with the exception that the necks for providing access to second chamber 28b and first chamber 16b are both located on the same end.

As shown in FIG. 6, roller bottle 10b preferably includes a generally cylindrical exterior receptacle 12b with a longitudinal axis C and a sidewall 14b. Exterior receptacle 12b preferably has a first chamber 16b within and first end 18b having a first neck 20b with a neck opening 22b therethrough providing fluid access to chamber 16b. Exterior receptacle 12b preferably includes a closed second end 24b.

Roller bottle 10b preferably includes a generally cylindrical interior container 26b having a second chamber 28b within and a longitudinal axis C'. Preferably interior container 26b is located coaxially within exterior receptacle 12b and has a first end 30b adjacent to first end 18b of exterior receptacle 12b and a closed second end 32b adjacent to second end 24b of the exterior receptacle. First end 30b of the interior container and first end 18b of the exterior receptacle preferably include a neck 34b having an opening 36b therethrough. Opening 36b is isolated from first chamber 16b, providing fluid access only to second chamber 28b.

Preferably bottle 10b is assembled by pre-assembling interior container 26b including second end 24b, interior container first end 30b and exterior receptacle first end 18b, then coaxially placing interior container 26b into exterior receptacle sidewall 14b having the exterior receptacle second end 24b bonded thereto. Preferably exterior receptacle first end 18b is then bonded to sidewall 14b to complete the assembly.

One skilled in the art of manufacture and in cell culture will recognize that, for particular applications, further preferred embodiments incorporating combinations of the preferred embodiments illustrated in FIGS. 1–6 are considered to be within the scope of the present invention.

What is claimed is:

1. A roller bottle comprising:

an exterior receptacle with a longitudinal axis having a first chamber surrounded by a sidewall, said sidewall having an interior surface and said exterior receptacle having a first neck at one end, said first neck having an opening therethrough providing fluid access to said first chamber;

an interior container with a longitudinal axis having a second chamber, said interior container being located coaxially within said exterior receptacle and having a second neck at one end, said second neck having an opening therethrough providing fluid access to said second chamber;

said exterior receptacle being formed from a material substantially impermeable to gas and liquid and being sealed in a substantially fluid tight fashion;

said interior container having at least a portion formed from a polymeric microporous material and being sealed in a substantially fluid tight fashion; and said roller bottle having a support for supporting said interior container a distance from said interior surface of said exterior receptacle.

2. The roller bottle of claim 1 wherein said interior container has a sidewall portion surrounding said second chamber and said sidewall portion is formed from said microporous material.

3. The roller bottle of claim 2 wherein said sidewall portion of said interior container has an outside surface and an inside surface said support including at least one helical spacer intermediate said outside surface of said interior container and said interior surface of said exterior receptacle which functions as an Archimedes screw when said roller bottle is horizontal, has a layer of liquid in said first chamber and is longitudinally rotated, thereby bathing said outside surface of said sidewall portion of said interior container with liquid from said first chamber.

4. A roller bottle comprising:

a generally cylindrical exterior receptacle having a longitudinal axis, a sidewall having an interior surface and a first chamber within having a first end and a second end, said first end having a first neck having an opening therethrough providing fluid access to said first chamber;

a generally cylindrical interior container having a second chamber and a longitudinal axis, said interior container being located coaxially within said exterior receptacle and having a closed first end adjacent said second end of said exterior receptacle, said second end of said exterior receptacle and said second end of said interior container each with a second neck having an opening isolated from said first chamber therethrough providing access to said second chamber;

said exterior receptacle being formed from a material being substantially impermeable to gas and liquid and being substantially sealed in fluid tight fashion at said first end and said second end thereby forming said first chamber having said fluid access from said first neck at said first end; and said interior container having a sidewall, at least a portion of said sidewall being formed from a polymeric microporous material, said interior container having a framework for supporting said interior container a distance from said inside surface of said sidewall of said exterior receptacle, and sidewall being sealed in a substantially fluid tight fashion at said first end and said second end of said interior container thereby forming said second chamber having said fluid access from said second neck at said interior container second end and through said membrane.

5. The roller bottle of claim 4 wherein said sidewall of said interior container has an outside surface and an inside surface and said sidewall of said exterior receptacle further includes an inside surface, said framework including at least one helical spacer intermediate said outside surface of said interior container and said inside surface of said exterior receptacle which functions as an Archimedes screw when said roller bottle is rotated about a longitudinal axis.

6. The roller bottle of claim 5 wherein said framework for supporting said interior container at said distance from said inside surface of said exterior receptacle comprises said first end of said interior container, said second end of said interior container, said helical spacer and a plurality of supports between said inside surface of said exterior receptacle and said interior container.

7. The roller bottle of claim 4 wherein said first neck at said first end of said exterior receptacle has threads for receiving a cap for sealing said first chamber and said second neck at said second end of said interior container has threads for receiving a cap for sealing said second chamber.

8. The roller bottle of claim 4 wherein said first end of said exterior receptacle and said second end of said exterior receptacle further include recessed portions having said necks recessed therein in said respective ends so that when said necks have said caps mounted thereon said caps are substantially within said recesses, thereby allowing said roller bottle to stand upright on said ends facilitating handling and fluid transfer.

9. The roller bottle of claim 4 wherein said first end of said interior container is recessed a distance from said first end of said exterior receptacle thereby providing a reservoir area at said first end of said exterior receptacle to facilitate fluid transfer into and from said first chamber.

10. The roller bottle of claim 4 wherein said interior container is removable from said exterior receptacle to facilitate a harvest of the cells being cultured on said inside surface of said sidewall of said exterior bottle.

11. The roller bottle of claim 10 wherein said second end of said exterior receptacle further comprises said second end of said interior container and said second end of said exterior receptacle is removable from said exterior receptacle, so that when said second end of said exterior receptacle is removed, said interior container is also removed from said exterior receptacle.

12. The roller bottle of claim 11 wherein said sidewall of said interior container further includes said sidewall being detachable from said first end and said second end of said interior container thereby facilitating dismounting said sidewall of said interior container to allow access to cells being cultured on said interior surface of said sidewall.

13. A roller bottle comprising:

a generally cylindrical exterior receptacle with a longitudinal axis having a sidewall having an interior surface and a first chamber within having a first end with a first neck having an opening therethrough providing fluid access to said first chamber and a second end;

a generally cylindrical interior container having second chamber and a longitudinal axis, said interior container being located coaxially within said exterior receptacle and having a first end adjacent said first end of said exterior bottle and a second end adjacent said second end of said exterior receptacle, said first end of said exterior receptacle and said first end of said interior container further including a second neck having a passageway therethrough for providing fluid access to said second chamber;

said exterior receptacle being formed from a material being substantially impermeable to gas and liquid and being sealed in a substantially fluid tight fashion at said first end and said second end thereby forming said first chamber having said fluid access from said first neck at said first end; and at least a portion of said interior container being formed from a polymeric microporous material, and said interior container being sealed in a substantially fluid tight fashion at said first end and said second end thereby forming said second chamber having said fluid access from said second neck;

said roller bottle having a support for supporting said interior container a distance from said interior surface of said exterior receptacle.

14. The roller bottle of claim 13 wherein said distance of said outside surface of said interior container from said interior surface of said sidewall of said exterior receptacle is between about 0.010 inches (0.254 millimeters) to about 0.40 inches (10.16 millimeters).

15. The roller bottle of claim 13 wherein said microporous material is a membrane formed from a material selected from the group consisting of polyethylene terephthalate and polycarbonate, said membrane having open pores therethrough sized between about 0.2 microns to about 10.0 microns and a pore density between about $0.1 \times 10^6$ to about $10.0 \times 10^6$ pores per square centimeter.

* * * * *